United States Patent [19]

Haugwitz et al.

[11] 4,218,396
[45] Aug. 19, 1980

[54] PHENYLENE-BIS (SUBSTITUTED THIOUREAS)

[75] Inventors: Rudiger D. Haugwitz; Barbara V. Maurer, both of Titusville, N.J.

[73] Assignee: E. R. Squibb & Sons, Inc., Princeton, N.J.

[21] Appl. No.: 727,835

[22] Filed: Sep. 29, 1976

[51] Int. Cl.$^2$ ............... A61K 31/17; C07C 157/09
[52] U.S. Cl. ............... 260/552 R; 260/465 D; 424/304; 424/322
[58] Field of Search ........... 260/552 R, 465 D, 553 A

[56] References Cited

U.S. PATENT DOCUMENTS

| | | | |
|---|---|---|---|
| 3,138,571 | 6/1964 | Popoff | 260/553 A X |
| 3,232,933 | 2/1966 | Gündel | 260/552 R X |
| 3,266,982 | 8/1966 | Popoff | 424/322 |
| 3,707,556 | 12/1972 | Teach | 260/552 R X |
| 3,867,426 | 2/1975 | Olin et al. | 260/553 A X |
| 3,897,493 | 7/1975 | Teach | 260/553 A |

FOREIGN PATENT DOCUMENTS

| | | | |
|---|---|---|---|
| 634690 | 1/1962 | Canada | 260/553 A |
| 2450414 | 4/1975 | Fed. Rep. of Germany | 260/552 R |

OTHER PUBLICATIONS

Yamezaki et al., CA 81:164731n (1974).
Vasilev et al., CA 76:69081p (1972).
Vasilev, CA 70:87180a (1969).
Ganapathi et al., CA 48:7564c (1953).

Primary Examiner—Thomas A. Waltz
Attorney, Agent, or Firm—Lawrence S. Levinson; Donald J. Barrack

[57] ABSTRACT

Compounds having the formula

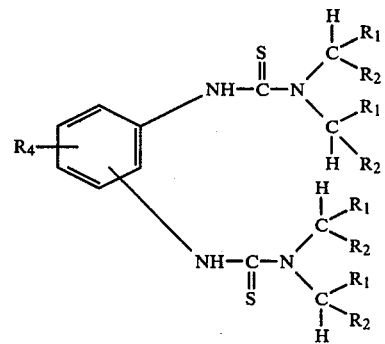

wherein $R_1$ and $R_2$ are each alkyl; and $R_4$ is hydrogen, halogen, trifluoromethyl, phenylthio, or cyano; have anthelmintic and anti-fungal activity.

4 Claims, No Drawings

PHENYLENE-BIS (SUBSTITUTED THIOUREAS)

BACKGROUND OF THE INVENTION

Certain arylthioureas have been disclosed as useful for the treatment of helminth infections in mammals. For example, U.S. Pat. No. 3,659,012 issued Apr. 25, 1972 to Porter et al., discloses that particular 1,1,3-trisubstituted thioureas are anthelmintic agents. Ticarbodine ($\alpha,\alpha,\alpha$-trifluoro-2,6-di(methyl)thio-1-piperidinecarboxy-m-toluide), has the structural formula

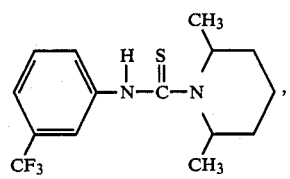

and has been reported to have a high degree of anthelmintic efficacy; see Am. H. Vet Res., 33 (4):709 (1972).

It has now been found that certain phenylene-bis[substituted thioureas] have anthelmintic activity.

BRIEF DESCRIPTION OF THE INVENTION

Compounds having the formula

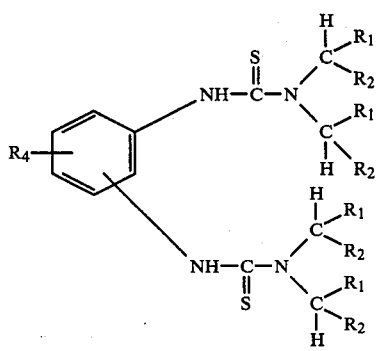

have useful anthelmintic and anti-fungal activity. In formula I, and throughout the specification, the symbols are as defined below.

$R_1$ and $R_2$ can be the same or different alkyl group;

$R_4$ can be hydrogen, halogen, trifluoromethyl, phenylthio, alkoxy or cyano.

The terms "alkyl" and "alkoxy" as used throughout the specification, refer to straight and branched chain groups having 1 to 4 carbon atoms.

The term "halogen", as used throughout the specification, refers to fluorine, chlorine, bromine and iodine.

DETAILED DESCRIPTION OF THE INVENTION

The phenylthioureas of this invention can be prepared by reacting an isothiocyanate having the formula

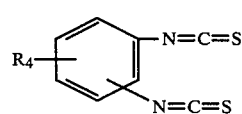

with a secondary amine having the formula

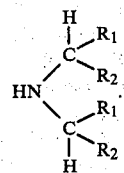

The reaction can be conveniently run in a variety of nonprotic solvents such as acetonitrile, ethyl ether, pyridine, benzene, ethyl acetate or chloroform. Reaction conditions are not critical, and can of course be varied as required for the particular isothiocyanate and amine being reacted.

Phenylenediisothiocyanates of formula II are known in the art; see, for example, Beilsteins Handbuch der Organischen Chemie, 23,23,50,105. They can be prepared in a two step procedure from dinitrobenzenes having the formula

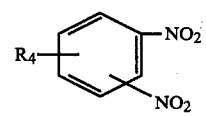

Hydrogenation of a dinitrobenzene of formula IV using art-recognized procedures yields the corresponding phenylenediamine having the formula

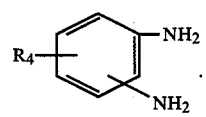

A phenylenediamine of formula V can be converted to the corresponding diisothiocyanate of formula II by reaction with a compound having the formula

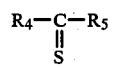

wherein $R_4$ is chlorine or bromine and $R_5$ is chlorine, bromine, or dialkylamino. Thiophosgene and N,N-diethylthiocarbamoyl chloride are preferred reagents.

When thiophosgene is employed in the above-described reaction, the reaction is preferably carried out in the presence of an acid binding agent, e.g., triethylamine. A further description of the above-described reaction can be found in Houben-Weyl's Methoden Der Organischen Chemie, 4th edition, volume 9, page 867 and footnotes (1955). The use of acid binding agents is further described by Schultz in Arch. Pharm., 295, 146-151 (1962).

When N,N-diethylthiocarbamoyl chloride is used to convert a compound of formula V to the corresponding diisothiocyanate, the reaction is carried out at an elevated temperature, preferably about 40° C. to about 200° C., as set forth in J. Org. Chem., 30, 2465 (1965).

Alternatively, the compounds of formula II can be prepared by reacting a phenylenediamine of formula V with carbon disulfide in the presence of an organic or inorganic base, whereby the phenylenediamine is first converted into the corresponding dithiocarbamate which is subsequently dehydrosulfurized to the corresponding diisothiocyanate. The dehydrosulfurization can be performed oxidatively with metal, e.g., lead, copper, zinc or ferric salts; iodine; an alkali metal hypochlorite or chlorite; an acid halide such as phosgene or phosphorous oxychloride; gaseous chlorine and ammonium sulfide; or chloramine-T.

Still another method for preparing the diisothiocyanates of formula II comprises reacting a phenylenediamine of formula V with carbon disulfide and dicyclohexylcarbodiimide in the presence of a tertiary amine according to the procedure set forth by Jochims, Chem. Ber., 101, 1746 (1968).

The phenylthioureas of formula I have useful anthelmintic activity, and more specifically, they have activity against gastrointestinal nematodes. They can be administered to mammalian species such as sheep, horses, dogs, and others, in an amount ranging from about 20 to 100 milligrams per kilogram of animal body weight per day to control nematocidal infestations. For this purpose, the compounds of this invention can be formulated according to conventional pharmaceutical practice.

Additionally, those compounds of this invention wherein $R_1$ and $R_2$ are alkyl exhibit anti-fungal activity against species of Trichophyton, e.g., *Trichophyton Mentagrophytes,* and Candida, e.g., *Candida Albicans,* and anti-protozoal activity against species of Trichomonas, e.g., *trichomonas Vaginalis.* Infections caused by these organisms can be treated with the compounds of this invention.

The following examples are specific embodiments of this invention.

EXAMPLE 1

N,N''-(1,4-Phenylene)bis[N',N'-bis(1-methylethyl)thiourea]

To a solution of 1.92 g. of 1,4-phenylenediisothiocyanate in 100 ml. of acetonitrile is added 2.5 g. of diisopropylamine. On standing, a precipitate forms which is filtered off and crystallized from acetone-cyclohexane to yield 2.7 g. of the title compound, melting point 185° C.

EXAMPLE 2

N,N''-(1,3-Phenylene)bis[N',N'-bis (1-methylethyl)thiourea]

To a solution of 3.84 g. of 1,3-phenylenediisothiocyanate in 100ml. of acetonitrile is added 4.4 g. of diisopropylamine and the mixture is refluxed for 3 hours. The solvent is removed in vacuo and the residue is crystallized from acetonitrile to yield 3.5 g. of the title compound, melting point 128°–129° C.

EXAMPLE 3

N,N''-(4-Fluoro-1,3-phenylene)bis[N',N'-bis-(1-methylethyl)thiourea]

To a solution of 4.2 g. of 2,4-diisothiocyanatofluorobenzene in 100 ml. of acetonitrile is added 4.1 g. of diisopropylamine and the mixture is refluxed for 3 hours. The solvent is removed in vacuo and the residue is crystallized from acetonitrile to yield 5.1 g. of the title compound, melting point 133°–135° C.

EXAMPLE 4

N,N''-(4-Methoxy-1,3-phenylene)bis[N',N'-bis-(1-methylethyl)thiourea]

A mixture of 4.4 g. of 2,4-diisothiocyanatomethoxybenzene and 4.1 g. of diisopropylamine is refluxed in 100 ml. of acetonitrile for 3 hours. The solvent is removed in vacuo and the residue is crystallized from acetonitrile to yield 4.7 g. of the title compound, melting point 127°–129° C.

EXAMPLE 5

N,N''-[4-Chloro-1,3-phenylene]bis[N',N'-bis-(1-methylethyl)thiourea]

A mixture of 11.1 g. of 4-chloro-1,3-diisothiocyanatobenzene and 10.2 g. of diisopropylamine is refluxed in 250 ml. of acetonitrile for 4 hours. The reaction mixture is cooled and the acetonitrile is removed in vacuo. The residue is crystallized twice from ether to yield 5.0 g. of the title compound, melting point 122°–123° C.

EXAMPLES 6–8

Following the procedure of Example 1, but substituting the compound listed in column I for 1,4-phenylenediisothiocyanate and the compound listed in column II for 2,6-dimethyl-1-piperidine, yields the compound listed in column III.

| Example | Column I | Column II | Column III |
| --- | --- | --- | --- |
| 6 | 2,4-diisothiocyanato-1-(phenylthio)benzene | diisopropylamine | N,N''-[4-(phenylthio)-1,3-phenylene]bis[N',N'-bis-(1-methylethyl)thiourea] |
| 7 | 2,4-diisothiocyanato-1-(trifluoromethyl)-benzene | diisopropylamine | N,N''-[4-(trifluoromethyl)-1,3-phenylene]bis[N',N'-bis-(1-methylethyl)thiourea] |
| 8 | 2,4-diisothiocyanatocyanobenzene | diisopropylamine | N,N''-(4-cyano-1,3-phenylene)-bis[N',N'-bis-(1-methylethyl)-thiourea] |

What is claimed is:

1. N,N''-[4-chloro-1,3-phenylene]bis[N',N'-bis-(1-methylethyl)thiourea].

2. N,N''-(1,3-phenylene)bis[N',N'-bis(1-methylethyl)thiourea].

3. N,N''-(4-fluoro-1,3-phenylene)bis[N',N'-bis-(1-methylethyl) thiourea].

4. N,N''-(4-methoxy-1,3-phenylene)bis[N',N'-bis-(1-methylethyl)thiourea].

* * * * *